US005248776A

United States Patent [19]
Chu et al.

[11] Patent Number: 5,248,776
[45] Date of Patent: Sep. 28, 1993

[54] PROCESS FOR ENANTIOMERICALLY PURE β-L-1,3-OXATHIOLANE NUCLEOSIDES

[76] Inventors: Chung K. Chu; Lak-Shin Jeong; J. Warren Beach, all of Athens, Ga.

[73] University of Georgia Research Foundation, Inc., Athens, Ga.

[21] Appl. No.: 803,086

[22] Filed: Dec. 5, 1991

Related U.S. Application Data

[63] Continuation-in-part of Ser. No. 699,197, May 13, 1991, which is a continuation-in-part of Ser. No. 622,762, Dec. 5, 1990.

[51] Int. Cl.$^5$ ............... C07D 473/32; C07D 405/04; A61K 31/505
[52] U.S. Cl. .................... 544/310; 544/182; 544/180; 544/265; 544/264; 544/276; 544/277; 544/298; 544/313; 544/315; 544/317
[58] Field of Search ............ 544/182, 180, 265, 264, 544/276, 277, 298, 310, 315, 313, 317

[56] References Cited

U.S. PATENT DOCUMENTS

5,041,449  8/1991  Belleau et al. ............ 514/274
5,047,407  9/1991  Belleau et al. ............ 514/274

FOREIGN PATENT DOCUMENTS

0337713  4/1989  European Pat. Off. .
0382526  2/1990  European Pat. Off. .

OTHER PUBLICATIONS

Chu, C. K. et al. *J. Med. Chem.*, 32, 612 (1989).
Erikkson, B. F. H., et al., *Antimicrob. Agents Chemother.*, 33, 10, 1729 (1989).
Lin, T. S. et al., *Biochem. Parmacol.*, 36 311 (1987).
Hamamoto, Y., et al., *Antimicrob. Agents Chemother.*, 31 907 (1987).
Balzarini, J., et al., *Biochem. Biophys. Res. Commun.*, 140, 735 (1987).
Martin, T. A. et al., *J. Med. Chem.*, 33, 2137 (1990).
Watanabe, K. A., et al., *J. Med. Chem.* 33, 2145 (1990).
Starzycki, R. Z., et al., *J. Med. Chem.*, 33, 2150 (1990).
Furman, P. A., et al., *Proc. Natl. Acad. Sci. U.S.A.*, 83, 8333 (1986).
Chan, Y. C., et al., *J. Biol. Chem.*, 262, 2187 (1987).
St. Clair, M. H., et al., *Antimicrob. Agents Chemother.*, 31, 1972 (1987).
Schinazi, R. F., et al., *Antimicrob. Agents Chemother.*, 33, 115 (1989).
Van Roay, P., et al., *J. Am. Chem. Soc.*, 110, 2277 (1988).
Van Roay, P., et al., *Proc. Natl. Acad. Sci. U.S.A.*, 86, 3929.
Norheck, D. W., et al., *Tet. Lett.*, 30, 6263 (1989).
Belleau, et al., *Fifth Intl. conf. on AIDS, Montreal, Canada*, paper No. T.C.01 (Jun. 4–9, 1990).
Lerner, J. M., et al., *J. Org. Chem.*, 33, 1780 (1968).
Evans, M. E., et al., *Carbohydrate Research* 28, 359 (1973).
Ishidate, M., et al., *Chem. Pharm. Bull.*, 13, 173 (1965).
Dhavale, D., et al., *Tet. Lett.*, 29, 6163 (1988).
Niedballa, et al., *J. Org. Chem.*, 39, 25 (1974).
Vorbruggen, et al., *Chem. Ber.*, 114, 1234–1255 (1981).

*Primary Examiner*—Cecilia Tsang

[57] ABSTRACT

An asymmetric process for the preparation of enantiomerically pure β-L-(−)-1,3-oxathiolane-nucleosides that includes the initial preparation of the key chiral intermediates (2R,5R) and (2R,5S)-5-(O-protected)-2-(protected-oxymethyl)-1,3-oxathiolane from 1,6-thioanhydro-L-gulose. The 2R,5(R,S)-5-(O-protected)-2-(protected-oxymethyl)-1,3-oxathiolane is condensed with a desired heterocyclic base, typically a purine or pyrimidine base, to provide the product nucleoside. The synthesis can be used to prepare the pharmaceutically important compound, β-L-(−)-1-[(2β,4β)-2-(hydroxymethyl)-4-(1,3-thioxolane)]cytosine (β-L-(−)BCH-189).

10 Claims, 4 Drawing Sheets

1, 3 - Oxathiolane Nucleoside wherein:

B = heterocyclic base
X = C4' chiral carbon atom
Y = C1' chiral carbon atom 1
(±)-BCH189
β-DL-(±)

2
β-D-(+)

3
β-L-(-)

4
α-D-(-)

5
α-L-(+)

PROCESS FOR ENANTIOMERICALLY PURE β-L-1,3-OXATHIOLANE NUCLEOSIDES

The government has rights in this invention by virtue of grants from the Public Health Service of the National Institute of Allergy and Infectious Diseases.

This application is a continuation-in-part of U.S. Ser. No. 07/699,197, filed on May 13, 1991, which is a continuation-in-part of U.S. Ser. No. 07/622,762, entitled "Enantiomerically Pure β-D-(−)-Dioxolane-Nucleosides," filed on Dec. 5, 1990, by Chung K. Chu and Raymond F. Schinazi, both of which are incorporated by reference.

SUMMARY OF THE INVENTION

This invention is in the area of the organic synthesis of nucleosides, and in particular relates to a process for the preparation of enantiomerically pure β-L-1,3-oxathiolane nucleosides.

A nucleoside is a molecule consisting of a 5-carbon sugar and a purine or pyrimidine base. Addition of a phosphate group to the 5'-position of the nucleoside converts the nucleoside into a nucleotide. Natural nucleotides are the building blocks for the nucleic acids, RNA (ribonucleic acid) and DNA (deoxyribonucleic acid).

In 1985, it was reported that the synthetic nucleoside 3'-azido-3'-deoxythymidine (AZT) inhibits the replication of human immunodeficiency virus type 1 (referred to below as HIV). Mitsuya, H., et al., *Proc. Natl. Acad. Sci. U.S.A.* 82, 7096 (1985). HIV is believed to be the etiological cause of acquired immunodeficiency syndrome (AIDS). Since then, a number of other synthetic nucleosides having anti-HIV activity have been identified, including 3'-azido-2',3'-dideoxyuridine (referred to as AZDU, or CS-87), 3'-azido-2',3'-dideoxycytidine (CS-91), 3'- azido-5-methyl-2',3'-dideoxycytidine (CS-92), 5-ethyl-3'-azido-2',3'- dideoxyuridine (CS-85), and 3'-fluoro-3'-deoxythymidine (FDT). In the 5'-triphosphorylated form, these nucleosides are known to inhibit HIV reverse transcriptase as well as cause chain-termination of the growing viral DNA chain.

AZT has been approved by the U.S. Food and Drug Administration for administration to patients with AIDS and AIDS-related complex. Several of the other synthetic nucleoside derivatives are undergoing various stages of clinical trials, including 2',3'-dideoxyuridine, 2',3'-dideoxyinosine, 2',3'-dideoxycytidine, 3'-deoxy-2',3'-didehydrothymidine, and 2'-fluoro-arabinofuranosyl-2'-3'-dideoxycytidine.

The stereochemistry of nucleoside derivatives play an important role in their biological activity. The C1' position of the ribose in the nucleoside (the carbon bound to the nitrogen of the heterocyclic base, see FIG. 1) is a chiral center because the carbon is attached to four different moieties. Likewise, there is an optically active center at C4' of the nucleoside (the ring carbon bound to the hydroxymethyl group that is phosphorylated in nucleotides). In the naturally occurring nucleosides, both the base attached to the C1' atom and the hydroxymethyl group attached to the C4' atom are on the same side of the carbohydrate ring.

A carbohydrate configuration in which the C1' and C4'-substituents are on the same side of the carbohydrate plane (i.e., the substituents are cis) is referred to as a "β-configuration." A carbohydrate configuration in which the C1' and C4'-substituents are on the opposite side of the carbohydrate plane (i.e., the substituents are trans) is referred to as an "α-configuration". Referring to compound 1 of FIG. 2, a nucleoside is designated a D-nucleoside if the non-hydrogen substituent attached to the C4'-atom is above the plane of the carbohydrate ring. The nucleoside is designated an L-nucleoside if the non-hydrogen substituent attached to the C4'-atom is below the plane of the carbohydrate ring.

The non-naturally occurring α-isomers of nucleosides (in which the C1' or C4' substituents are on opposite sides of the carbohydrate plane) are rarely biologically active, and are typically toxic.

An analysis of the solid-state conformations of six active and two inactive anti-HIV nucleoside agents was recently performed to attempt to correlate the presence or absence of certain stereochemical features with high anti-HIV activity. Van Roey, P., et al., *J. Am. Chem. Soc.*, 1988, 110, 2277; and Van Roey, P., et al., *Proc. Natl. Acad. Sci. U.S.A.*, 1989, 86, 3929. The x-ray structures indicated that active anti-HIV nucleosides assume the C3'-exo or similar carbohydrate conformations while inactive compounds prefer the C3'-endo conformation. (Endo and exo refer to the conformations in which the atoms are at the same or opposite side of the sugar ring in relation to the base). The C3'-exo and C3'-endo conformations place the C5' atom in axial and equatorial positions, respectively. The position of the C5' atom affects the location of the 5'-hydroxyl group in relation to the base. Since the 5'-hydroxyl group is the site of phosphorylation of the nucleoside, its location with respect to the rest of the nucleoside is important.

Recently, several unusual types of nucleosides have been shown to be potent antiviral agents, including (±)-1-(1,3-oxothiolany)-cytosine (also referred to as (±) BCH-189), (−)-1-[(2β,4β)-2-(hydroxymethyl)-4-dioxolanyl]thymine (also referred to as dioxolane-T), oxetanocin, 6-phenylthio-uracilacyclonucleosides, and cyclobutane carbocyclic nucleosides. BCH-189 (a 1,3-oxathiolane nucleoside) and dioxolane-T are particularly interesting in that the 3'-$CH_2$ groups of the ribose moieties of these nucleosides are replaced by sulfur and oxygen atoms, respectively, as shown in FIG. 1.

Norbeck, D. W., at al., in *Tet. Lett.*, 1989, 30, 6263, reported a synthesis of (±)-dioxolane-T, that results in a racemic mixture of enantiomers about the C4' atom. The product was synthesized in five steps from benzyloxyaldehyde dimethylacetal and (±)-methyl glycerate to produce a 79% yield of a 1:1 diastereomeric mixture. The X-ray crystallographic analysis of the product revealed that the dioxolane ring adopts the $^3T_4$ conformation commonly observed in ribonucleosides, with the O3' atom in the endo position. Norbeck reported that the racemic mixture of dioxolane-T exhibits an anti-HIV activity of 20 μM in ATH8 cells, and attributed the low efficacy against the virus to an effect of the endo conformation of the O3' atom.

U.S. Ser. No. 07/622,762 entitled "Enantiomerically Pure β-D-(−)-Dioxolane-Nucleosides," filed on Dec. 5, 1990, by Chung K. Chu and Raymond F. Schinazi, discloses a synthesis of enantiomerically pure β-(−)-dioxolane-nucleosides (dioxolane nucleosides in which both the substituents in the C1' and the C4' position are in the β-position) from D-mannose via 1,6-anhydro-D-mannose. The anti-HIV activity enantiomerically pure β-D-(−)-dioxolane-T in peripheral blood mononuclear cells was measured at 0.3 μM indicating that the naturally occurring enantiomerically pure βnucleoside is substantially more active than the prior known racemic mixture that included the nonnaturally-occurring isomer. The enantiomerically pure nucleoside is also less toxic than the racemic mixture, presumably because of the absence of the nonnaturally occurring derivative.

Belleau, et al., in the Fifth International Conf. on AIDS, Montreal, Canada June 4-9, 1990, paper No. T.C.O.1., reported a method of synthesis of cytidine nucleosides that contain oxygen or sulfur in the 3'-position. The dioxolane ring was prepared by the condensation of $RCO_2CH_2CHO$ with glycerine. As with the Norbeck synthesis, the Belleau synthesis results in a racemic mixture about the C4'-carbon of the nucleoside. ($\pm$)BCH-189 (referred to by Belleau as NGBP-21) has been shown to have a potent anti-HIV activity ($EC_{50}$=0.03, 0.2 and 0.05 $\mu$M in CEM, MT4, and PBM cells, respectively) with an excellent bone marrow toxicity profile. ($\pm$)-BCH-189 is currently undergoing preclinical toxicology.

U.S. Ser. No. 07/699,197, filed on May 13, 1991, described a synthesis of $\beta$-D-(+)-1-[(2$\beta$,4$\beta$)-2-(hydroxymethyl)-4-(1,3-oxathiolane)]cytosine from 1,6-thioanhydro-D-mannose. Since the $\beta$-D isomers of nucleosides are in general the biologically active isomers, it was expected that this form of BCH-189 would exhibit the highest activity of the BCH-189 enantiomers. Surprisingly, it was found that the $\beta$-D-(+) isomer 2 ($EC_{50}$=0.32 $\mu$M) was significantly less potent than the racemic ($\pm$) BCH-189 1 ($EC_{50}$=0.06 $\mu$M) in human peripheral blood mononuclear (PBM) cells. Furthermore, the $\beta$-D-(+) isomer 2 was found to be inactive against HBV (Hepatitis B Virus), while the racemic mixture was found to have HBV activity. In light of this information, it was desired to synthesize the $\beta$-L-(−) 3 and the $\alpha$-L-(+) 5 isomers and compare their anti-HIV and anti-HBV activities to those of ($\pm$) BCH-189.

There is also a need for a synthesis of $\beta$-L-(−)-1,3-oxathiolane nucleosides in general as a research tool to provide more information on the effect of stereochemistry on the antiviral activity of nucleoside derivatives, and to provide new anti-HIV agents.

It is therefore an object of the present invention to provide a method of synthesis of enantiomerically pure $\beta$-L-1,3-oxathiolane nucleosides.

SUMMARY OF THE INVENTION

An asymmetric process for the preparation of enantiomerically pure $\beta$-L-(−)-1,3-oxathiolane-nucleosides is presented. The process involves the initial preparation of the key chiral intermediate 2R,5(R,S)-5-(O-protected)-2-(protected-oxymethyl)-1,3-oxathiolane from 1,6-thioanhydro-L-gulose, a sugar that has the required stereochemistry for the production of the $\beta$-L-(−)-1,3-oxathiolane nucleoside, including the correct diastereomeric configuration about the 2 position of the sugar (that becomes the 4'-position in the later formed nucleoside). 1,6-Thioanhydro-L-gulose is easily prepared from L-gulose.

The 2R,5(R,S)-5-(O-protected)-2-(protected-oxymethyl)-1,3-oxathiolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure $\beta$-L-(−)-1,3-oxathiolane-nucleoside.

Products made according to this process can be used as a research tool to study the inhibition of HIV in vitro or can be administered in a pharmaceutical composition to inhibit the growth of HIV in vivo.

The process described herein can be used to prepare the pharmaceutically important compound, $\beta$-L-(−)-1-[(2$\beta$,4$\beta$)-2-(hydroxymethyl)-4-(1,3-oxathiolane)]cytosine ($\beta$-L-(−)BCH-189).

As an example (see FIGS. 3 and 4), synthesis of 1,6-thioanhydro-L-gulose 9 was accomplished in 4 steps from L-gulose 6. Selective 6-O-tosylation followed by acetylation gave 1,2,3,4-tetra-O-acetyl-6-O-tosyl-L-gulose 7 as a foam in 96.7% yield. Treatment of 7 with 3 molar equivalents of HBr/AcOH (45% w/v) using acetic acid as solvent gave the bromo sugar 8 (99%). Reaction of the bromo sugar 8 with 3.3 molar equivalent of potassium O-ethylxanthate in refluxing acetone gave 2,3,4-tri-O-acetyl-1,6-thioanhydro-L-gulose, which was not isolated, but was deacetylated using $NH_4OH$/MeOH to give 1,6-thioanhydro-L-gulose 9 (72% from 8) as a crystalline solid. Treatment of 9 with $NaIC_4$ at −10° C. was carried out to cleave the 2,3-cis diol, and then the resulting aldehyde (2-formyl-5-(2'-(2'-hydroxyacetaldehyde)-1,3-oxathiolane) was reduced with $NaBH_4$. The vicinal diol (2-hydroxymethyl-5-(2'-(1',2'-dihydroxyethyl)-1,3-oxathiolane) was protected as the isopropylidine derivative 10 (60%). Silylation of the remaining primary alcohol followed by treatment with 10% HCl in MeOH at −10° C. gave protected diol 11. Oxidative cleavage of the resulting diol 11 with $Pb(OAc)_4$ followed by further oxidation with pyridinium dichromate (PDC) in DMF gave the acid 12 without oxidation of the ring sulfide group to the sulfoxide. Oxidative decarboxylation of 12 using $Pb(OAc)_4$/pyridine in dry THF gave the acetate 13 (66% from 11). Condensation of 13 with silylated N-acetylcytosine in dry 1,2-dichloroethane using trimethylsilyl triflate as the Lewis acid catalyst gave an $\alpha$,$\beta$-mixture 1:2) of 14 and 15 (64%). Separation of the anomers by silica gel chromatography followed by deacetylation using $NH_3$/MeOH and desilylation using tetra-n-butylammonium fluoride gave the final compounds, $\beta$-L-(−) isomer 3 and $\alpha$-L-(+) isomer 5, respectively.

DETAILED DESCRIPTION OF THE INVENTION

As used herein, the term "protected" refers to a moiety that has been placed on a functional group of a molecule to prevent further reaction of the moiety during derivatization of another portion of the molecule. Protecting groups, particularly for oxygen and nitrogen, are well known to those skilled in the art of organic chemistry.

Figure 1:
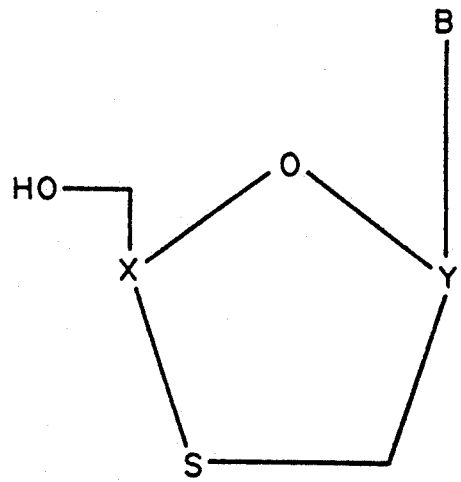
FIG. 1 is an illustration of a 1,3-oxathiolane nucleoside with the C1' and C4' chiral carbon atoms indicated by asterisk.
Figure 2:
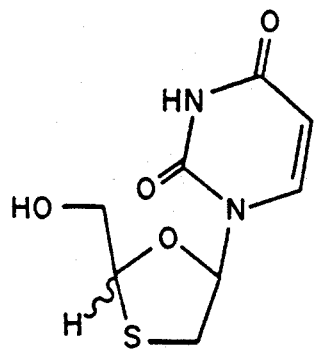
FIG. 2 is an illustration of the $\beta$-D-(+) and $\beta$-L-(−) isomers of 1-[(2$\beta$,4$\beta$)-2-(hydroxymethyl)-4-(1,3-Oxathiolane)]cytosine (BCH-189).
Figure 2:
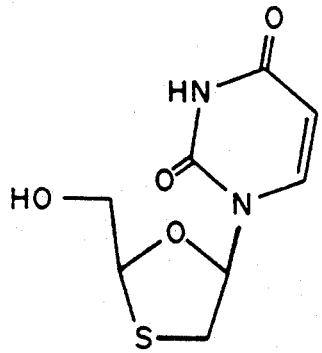
Figure 2:
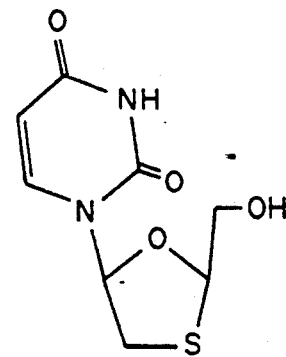
Figure 2:
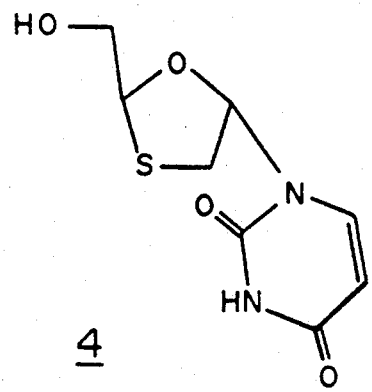
Figure 2:
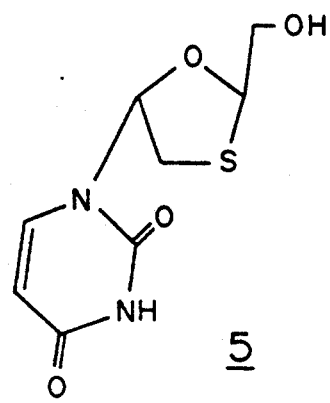

The term "1,3-oxathiolane nucleoside" as used herein refers to a nucleoside derivative as depicted in FIGS. 1 and 2, wherein a 1,3-oxathiolane is attached to a heterocyclic base, typically a purine or pyrimidine base, through the oxathiolane C5 carbon (that becomes the C1'-carbon in the nucleoside).

The process for the preparation of enantiomerically pure β-L-(−)-1,3-oxathiolane nucleosides proceeds in two stages. In the first stage, a 1,3-oxathiolane derivative is prepared that includes a hydroxymethyl group in the chiral 2-position (that will become the hydroxymethyl group in the C4' position of the nucleoside) with the proper stereochemistry for the final enantiomerically pure β-L-(−)-nucleoside. In the second stage, the 1,3-oxathiolane is condensed with a heterocyclic base at the C5 position to produce a 1,3-oxathiolane nucleoside that has both the C1' (heterocyclic base) and the C4' (hydroxymethyl) substituents in the desired position.

Figure 3:
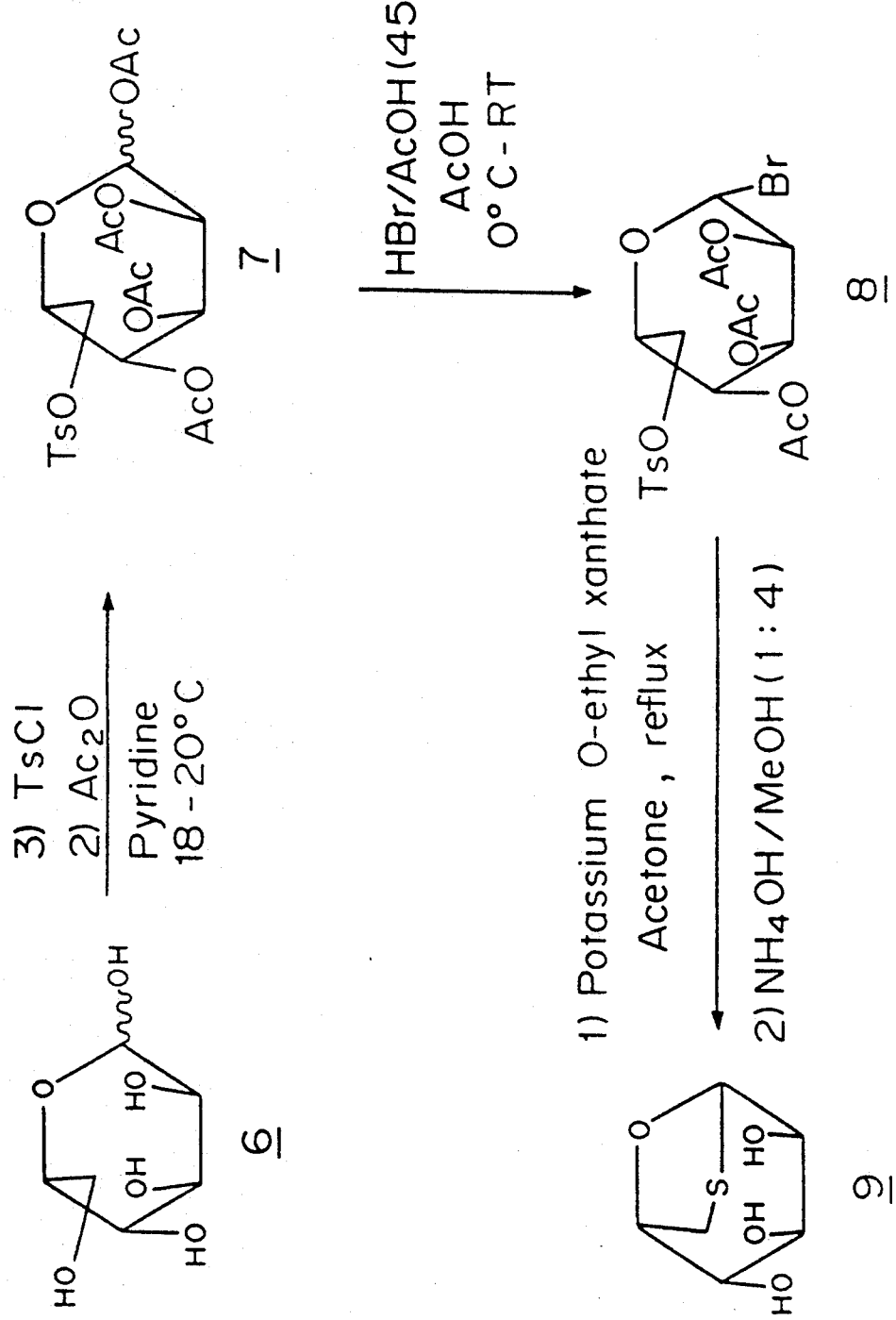
FIG. 3 is an illustration of the process for the preparation of 1,6-dideoxy-1,6-thioanhydro-L-gulose.
Figure 4:
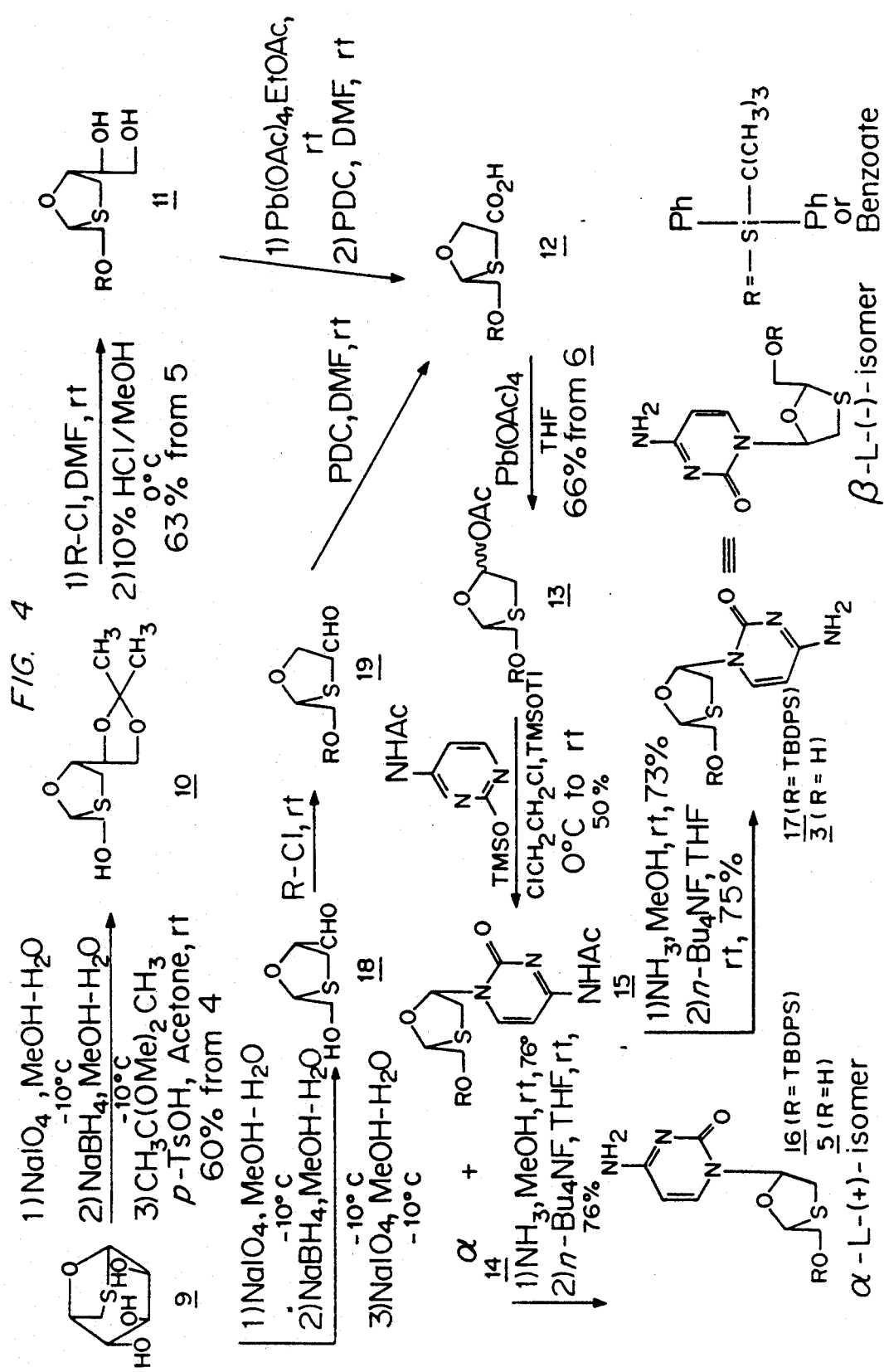
FIG. 4 is an illustration of the process for the preparation of $\beta$-L-(−)-1-[(2$\beta$,4$\beta$)-2-(hydroxymethyl)-4-(1,3-oxathiolane)]cytosine.

The compounds referred to below are numbered as illustrated in FIGS. 2, 3, and 4.

A. Preparation of 1,3-Oxathiolane Derivative

Preparation of 1,6-Thioanhydro-L-gulose

The starting material for this process for the preparation of enantiomerically pure β-L-(−)-1,3-oxathiolane nucleosides is 1,6-thioanhydro-L-gulose (FIG. 3, compound 9), that has the appropriate chiral center at C2 for the preparation of the desired β-L-(−)-(1,3)-oxathiolane nucleosides.

1,6-Thioanhydro-L-gulose can be prepared from L-gulose (FIG. 3, compound 6) in 3 steps (FIG. 3). L-Gulose can be prepared from L-gulonolactone, that in turn can be prepared from D-glucurono-6,3-lactone that is readily available and inexpensive. Lerner, L. M., et al., *J. Org. Chem.* 33, 1780 (1968); Evans, M. E., et al., *Carbohydrate Research* 28, 359 (1973); and Ishidate, M., et al., *Chem. Pharm. Bull.* 13, 173 (1965).

In the first step, the hydroxyl groups in gulose are protected. Taking advantage of the principle that reactivity in tosylation, and in esterification generally, decreases in the order primary alcohol>secondary alcohol>tertiary alcohol, the primary hydroxyl group at $C_6$ is initially selectively tosylated. The temperature used for this initial protecting step should be the lowest that allows for $C_6$ esterification without reaction of the other four hydroxyl groups in the molecule, preferably between 18 degrees and 20 degrees C. Tosylation can be performed with p-toluenesulfonyl chloride and pyridine, or under other conditions known to those in the art. After the $C_6$-hydroxyl group is protected, the other four hydroxyl groups are protected, preferably with an acetyl moiety, to provide 1,2,3,4-tetra-0-(protected)-6-0-(protected)-L-gulopyranoside 2. Other suitable oxygen protecting groups are known to those skilled in the art, and include benzoate. This reaction should be performed at the lowest temperature under which reaction occurs, preferably between 18 degrees and 20 degrees C.

In the second step according to this procedure, the 1-position of 1,2,3,4-tetra-0-(protected)-L-gulopyrannoside 2 is converted to 2,3,4-tri-0-(protected)-1-halo-6-0-(protected)-α-L-gulopyranoside 3 by reaction with HX, wherein X is bromo or chloro. In a preferred embodiment, the reaction is performed in acetic acid at a temperature range of between 0 degrees and 25 degrees C, for a time period of between six and eight hours.

In the third step, the gulopyranoside 8 is easily converted to 2,3,4-tri-0-(protected)-1,6-dideoxy-1,6-thioanhydro-L-gulose by reaction with potassium 0-ethyl xanthate, which can be purchased commercially from Aldrich Chemical Company, or prepared from KOH and carbon disulfide in ethanol. Alternatively, NaSH or $(Na)_2S$ can be used. The reaction is easily carried out in refluxing acetone. Typically, between 3.0 and 3.5 equivalents of xanthate reagent are used.

In the fourth step, 2,3,4-tri-0-(protected)-1,6-dideoxy1,6-thioanhydro-L-gulose is then deprotected under basic conditions at ambient temperature to provide 1,6-thioanhydro-L-gulose 9. Any base is suitable in this deprotection step, including ammonium hydroxide, sodium hydroxide, potassium hydroxide, and sodium methoxide. It is preferred that the pH be maintained at less than 9.

In preparing these enantiomerically pure β-L-1,3-oxathiolane nucleosides, care should be taken to avoid strong acidic conditions that would cleave the 1,3-oxathiolane ring. Reactions should be performed, if possible, in basic or neutral conditions, and when acidic conditions are necessary, the time of reaction should be minimized.

Conversion of 1,6-Thioanhydro-L-Gulose to 1,3-Oxathiolane Derivatives

According to this process, 1,6-thioanhydro-L-gulose 9 is easily converted to a 1,3-oxathiolane derivative via direct cleavage of the unprotected thioanhydro-L-gulose followed by reduction to the corresponding diol, isopropylidenation of the diol, silylation of the 2-hydroxymethyl group, and deisopropylidenation (see FIG. 4), or by initial isopropylidenation of 1,6-thioanhydro-L-gulose, protection of the remaining 4-hydroxyl group, deisopropylidenation of the diol, oxidation of the diol to a dialdehyde, and reduction of the dialdehyde, followed by protection of the 2-hydroxymethyl group with t-butyldiphenylsilyl and treatment with base (see FIG. 5).

Method of Conversion Illustrated in FIG. 4

As illustrated in FIG. 4, in one method, 1,6-thioanhydro-L-gulose 9 is initially oxidized with $NaIO_4$ or other oxidizing agent, including $KIO_4$ or $Pb(OAc)_4$, at low temperature (usually 0° to −20° C., and typically approximately −10° C.), in a suitable solvent such as methanol/water, to cleave the 2,3-cis diol. The resulting dialdehyde is then reduced with $NaBH_4$ or any borohydride to provide the corresponding vicinal diol. The diol is then protected, preferably with an isopropylidene group, using, for example, $CH_3C(OCH_3)_2CH_3$ and p-toluenesulfonic acid at room temperature. The reaction can also be performed with acetone and p-toluenesulfonic acid, optionally with cupric sulfate at room temperature. The hydroxymethyl group of the isopropylidene derivative 10 is then protected using methods known to those skilled in the art, typically with t-butyldiphenylsilyl chloride in DMF at room temperature, and then the diol is deprotected to form compound 11. Other protecting groups known to those skilled in the art can also be used.

Alternatively, compound 9, 1,6-dideoxy-1,6-thioanhydro-L-gulose can be converted to compound 18 (2R,5S)-5-formyl-2-hydroxymethyl-5-1,3-oxathiolane by: (1) oxidation with $NaIO_4$ at low temperature (typically dropwise addition of $NaIO_4$ at −10° C. over 20 minutes, with additional stirring for ten minutes) followed by (2) reduction with $NaBH_4$ or any borohydride under similar conditions as used for 10 to provide the corresponding diol, which, without isolation, is (3) further treated with $NaIO_4$.

The primary hydroxyl group of the aldehyde 18 is protected with a benzoyl or silyl group to give 19, which on treatment with pyridinium dichromate to afford the common intermediate 12, (2R,5S)-2-(protected-oxymethyl)-1,3-oxathiolane-5-carboxylic acid.

Method of Conversion Illustrated in FIG. 5

In the first step, the cis-hydroxyl groups of 9 are selectively protected, preferably with an isopropylidene group, to provide 2,3-0-(diprotected)-1,6-thioanhydro-L-gulose 20. The isopropylidene derivative can be prepared with dimethoxypropane and p-toluenesulfonic acid. The 2,3-0-(diprotected)-1,6-thioanhydro-L-gulose 20 without isolation is then protected at the 4-position (see FIG. 5). A preferred protecting group is benzoyl, however, other protecting groups known to those skilled in the art can also be used. The isopropylidene or other protecting group on the 2 and 3 hydroxyl groups is then removed with catalytic amounts of an acid such as sulfuric acid, hydrochloric acid, formic acid, trifluoroacetic acid, or sulfamic acid in 60% aqueous dioxane or other suitable solvent typically at a temperature range of approximately 0° to 75° C. to give 4-0-benzoyl-1,6-thioanhydro-L-gulose 22 in high yield as a solid. The cis diol of 22 is oxidatively cleaved to the dialdehyde 23 using lead tetraacetate in ethyl acetate. The dialdehyde 23 is reduced using sodium borohydride to give 24 which is protected at the 2-hydroxymethyl by a t-butyldiphenylsilyl group to give 25. Treatment of 25 with ammonium hydroxide affords 11.

Compound 12 is used in a modified Hunsdiecker reaction (Dhavale, D.; et al., *Tetrahedron Lett.*, 1988, 29, 6163) with Pb(OAc)$_4$ to provide the corresponding key chiral intermediates (2R,5R)- and (2R,5S)-5-acetoxy-2-(protected-oxymethyl)-1,3-oxathiolane (see compounds 13, FIG. 4) in good yield.

B. Condensation of a Heterocyclic Base with the 1,3-oxathiolane Derivative

In the next stage of this process for the preparation of enantiomerically pure 1,3-oxathiolane nucleosides, the key chiral intermediates (2R,5R)- and (2R,5S)-5-acetoxy-2-(protected-oxymethyl)-1,3-oxathiolane (see compounds 13, FIG. 4) are condensed with a protected heterocyclic base in the presence of trimethylsilyl triflate (trimethylsilyl trifluoromethanesulfonate) or a Lewis acid in a dry organic solvent to provide a mixture of 1'-α and 1'-β nucleosides that can be separated chromatographically or by other methods known to those in the art. The choice of catalyst for condensation may affect the final product ratio of α to β nucleoside product.

Any compound containing a nitrogen that is capable of reaction with a center of electron deficiency can be used in the condensation reaction. Purine bases include adenine, hypoxanthine, guanine, $N^6$-alkylpurines, $N^6$-benzylpurine, 6-halopurine, purine, $N^6$-acyl purine, 6-hydroxyalkyl purine, and 6-thioalkyl purine. Pyrimidine bases include thymine, cytosine, 5-azapyrimidine, 2-mercaptopyrimidine, uracil, 5-alkylpyrimidines, 5-benzylpyrimidines, 5-halopyrimidines, including 5-fluoropyrimidines such as 5-fluorocytidine, 5-vinylpyrimidine, 5-acetylenic pyrimidine, 5-acyl pyrimidine, 5-hydroxyalkyl pyrimidine, 5-thioalkyl pyrimidine, 6-thiophenyl and 6-selenylphenyl pyrimidines.

Functional oxygen and nitrogen groups on the heterocyclic base should be protected before condensation with the sugar. Protecting groups are well known to those skilled in the art, and include trimethylsilyl, dimethylhexylsilyl, and t-butyldiphenylsilyl, tritylmethyl, alkyl groups, acyl groups such as acetyl and propionyl, methylsulfonyl, and p-toluylsulfonyl.

Friedel-Crafts catalysts (Lewis acids) that can be used in the condensation reaction include $SnCl_4$, $ZnCl_4$, $TiCl_4$, $AlCl_3$, $FeCl_3$, $BF_3$-diethylether, and $BCl_3$. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Anhydrous aluminum chloride is not soluble in carbon disulfide. Niedballa, et al., *J. Org. Chem.* 39, 25 (1974). The preferred catalyst in $SnCl_4$. Useful solvents are 1,2-dichloroethane and methylene chloride.

Trimethylsilyl triflate can be used under the same conditions described above for the Friedel-Crafts catalysts. The reaction proceeds at a temperature range of from −10° C. to 200° C.

In the final step of this method of preparation of enantiomerically pure β-L-(−)-1,3-oxathiolane-nucleosides, the 5'-0-position of the nucleoside is deprotected. Desilylation can be carried out with a variety of reagents, including acetic acid, trifluoroacetic acid, hydrogen fluoride, n-tetrabutylammonium fluoride, potassium fluoride and pyridinium HCl. Acetic acid is preferred for commercial scale use because it is inexpensive. Other reagents for desilylation are known to those skilled in the art. Deacylation is accomplished in acid or base. 5-0-Ethers can be cleaved with $BCl_3$ or trimethylsilyl iodide.

The method of preparation of enantiomerically pure β-L-(−)-1,3-oxathiolane-nucleosides is further illustrated in the following working example for the preparation of β-L-(−)-1-[(2β,4β)-2-(hydroxymethyl)-4-(1,3-oxathiolane)]cytosine (BCH-189). The enumeration of compounds in the working examples refer to structures set out in FIGS. 3 and 4.

1,2,3,4-Tetra-0-acetyl-6-0-tosyl-L-gulopyranoside 7

To a suspension of L-gulose 6 (48.7 g, 0.27 mol) in dry pyridine (450 mL) was added dropwise a solution of p-toluenesulfonyl chloride (77.1 g, 0.405 mol, 1.5 eq) in pyridine (300 mL). The internal temperature was maintained between 18°–20° C. during the addition using an ice bath. On completion of addition the reaction was allowed to rise to room temperature and stirring continued until TLC indicated the absence of starting material (4 h). The reaction mixture was cooled and acetic anhydride (142 mL, 1.29 mol, 4.8 eq) was added dropwise, again maintaining the internal temperature between 18°–20° C. On completion of addition the reaction mixture was allowed to come to room temperature and stirred for 4 hr. The reaction mixture was concentrated under reduced pressure and the residue partitioned between ethyl acetate and water. The organic layer was washed with 1% aq $H_2SO_4$(2×), $H_2O$, and sat. aq $NaHCO_3$ solution (2×), dried ($MgSO_4$) filtered and concentrated. The residue was dried at high vacuum to give 7 (135.84 g, 96.7%) as a foam which was used in the next step without further purification.

2,3,4-Tri-0-acetyl-1-bromo-6-0-tosyl-α-L-gulopyranoside 8

To a 1 L round bottom flask containing 7(132 g, 0.25 mol) in acetic acid, cooled in an ice water bath was added HBr in acetic acid (45% w/v, 136 mL, 3 eq.). The flask was fitted with a $CaCl_2$ tube and stirred in the ice bath for 30 min. and then at room temperature for 15 h. The solvent was removed under reduced pressure and the residue partitioned between ethyl ether and cold water. The organic layer was washed twice with cold water and twice with cold sat. aq $NaHCO_3$ solution, dried ($MgSO_4$), filtered and concentrated. The residue was dried at high vacuum to give 8 (136.6 g, 99%) as a hygroscopic foam which was used without further purification.

1,6, Dideoxy-1,6-thioanhydro-L-gulose 9

To a solution of 8 (136.6 g, 0.261 mol) in acetone (1 L) was added potassium 0-ethyl xanthate (134 g, 0.835 mol, 3.2 eq.) and the reaction mixture was refluxed for 3 hours at which time TLC indicated complete disappearance of starting material and the thioanhydro triacetate. The reaction mixture was cooled and the solid filtered. The filtrate was concentrated and the residue partitioned between water and chloroform. The chloroform layer was washed with water, sat. sodium bicarbonate solution and brine, dried, filtered and concentrated. The residue was dissolved in methanol and treated with conc. ammonium hydroxide solution (4:1) and allowed to stir overnight. The reaction mixture was concentrated and the residue chromatographed over silica gel using 7% MeOH in chloroform as eluant to give 9 (33.4 g, 72%) as a crystalline solid from isopropanol. NMR (DMSOd6) δ 2.8 (dd, J=6.6 and 10.1 Hz, 1 H, 6a-H), 3.1 (d, J=10.1 Hz, 1 H, 6b-H), 3.4–3.8 (complex multip., 3H, 2-H,3-H,4-H), 4.5 (d, J=5 Hz, 1 H OH), 4.55 (dd, J=5.94 and 6.37 Hz, 1 H, 5-H), 4.82 (d, J=4.6 Hz, 1 H, OH), 5.1 (d, J=4.4 Hz, 1 H, OH), 5.35 (d, J=2.2 Hz, 1 H, 1-H). $[α]_D$=79.2 (c 1.06, MeOH); Anal. Calcd for $C_6H_{10}O_4S$: C, 40.4; H, 5.66; S, 17.99. Found: C, 40.42; H, 5.67; S, 17.89.

(1'S,2R,5R)-2-hydroxymethyl-5-(1',2'-0-isopropylidene)ethyl-1,3-oxathiolane 10.

To a solution of 9 (1.8 g, 10.11 mmol) in MeOH (30 mL), an aqueous solution (30 mL) of $NaIO_4$ (2.99 g, 14.15 mmol) was added dropwise at −10° C. over 20 min and the mixture was stirred at −10° C. for 10 min. $NaBH_4$ was added and the mixture was further stirred at −10° C. for 10 min. After filtration, the filtrate was neutralized with glacial acetic acid at 0° C. and solvents were evaporated. The residue was filtered through a short silica gel pad using $CHCl_3$-MeOH (10:1) as an eluent to remove inorganic salts. Solvents were evaporated and the residue was treated with acetone (150 mL), 2,2-dimethoxypropane (20 mL) and p-TsOH.$H_2O$ (2.01 g, 10.11 mmol) and stirred at room temperature for 1 hour. The mixture was neutralized with triethylamine, filtered and evaporated. The residue was dissolved in EtOAc (150 mL), washed with $H_2O$ and brine, dried ($MgSO_4$) and evaporated to give a crude residue which was purified by silica gel column chromatography (hexanes:ethyl acetate=1:1) to yield isopropylidene 10 (1.33 g, 60%) as a colorless syrup.

$^1$H NMR (CDCl$_3$) δ 1.38 and 1.45 (2×s, 6 H, isopropyl), 2.35 (br s, 1H, OH), 2.83 (dd, J=10.2 and 3.96 Hz, 1 H, 4-$H_a$), 2.98 (dd, J=5.49 and 1.76 Hz, 1 H, 4-$H_b$), 3.85 (dd, J=6.59 and 6.15 Hz, 2 H, $CH_2$—OH), 4.04 (ddd, J=3.08, 2.42 and 1.76 Hz, 2 H, 2'-$CH_2$—O), 4.15 (dd, J=4.18 and 3.73 Hz, 1 H, 5-H), 4.30 (dd, J=6.37 and 6.38 Hz, 1 H, 1'-CH), 5.33 (dd, J=3.53 and 3.53 Hz, 1 H, 2-H).

(1'S,2R,5R)-2-(t-Butyldiphenylsiloxymethyl)-5-(1'-2'-dihydroxy)ethyl -1,3-oxathiolane 11.

To a solution of 10 (1.5 g, 6.82 mmol) in DMF (20 mL), imidazole (0.928 g, 13.64 mmol) and tert-butyldiphenylsilyl chloride (2.66 mL, 10.23 mmol) were added and the mixture was stirred at room temperature for 1 hour. DMF was evaporated and the residue was dissolved in EtOAc (150 mL), washed with $H_2O$ and brine, dried ($MgSO_4$) and evaporated to give a crude residue, which, without further purification, was treated with 10% HCl in MeOH (20 mL v/v) at 0° C. and stirred for 30 min. The mixture was neutralized with $NaHCO_3$, diluted with EtOAc (200 mL) and separated. The aqueous layer was extracted with EtOAc (150 mL×2) and the combined organic layers were washed with water and brine, dried ($MgSO_4$), evaporated to give a residue which was purified by silica gel column chromatography to give protected diol 11 (1.8 g, 63.4%) as a colorless syrup.

$^1$H NMR(DMSO-d$_6$) δ 1.00 (s, 9 H, t-butyl), 2.82 (d, J=7.5 Hz, 1 H, 4-$H_a$), 2.98 (dd, J=3.75 and 7.5 Hz, 1 H, 4-$H_b$), 3.45 (m, 2 H, 2-$CH_2$—OSi), 3.5–4.4 (m, 4 H, 1'-H, 2'-H and 5-H), 4.58 (t, J=5.27 Hz, 1 H, 2'-$CH_2OH$), 4.77 (d, J=5.49 Hz, 1 H, 1'-CHOH), 5.22 (t, J=5.5 Hz, 1 H, 2-H), 7.37–7.72 (m, 10 H, 2×$C_6H_5$).

(2R,5(R,S))-5-Acetoxy-2-(t-butyldiphenylsiloxymethyl)-1,3-oxathiolane 13.

To a solution of 11 (0.9 g, 2.15 mmol) in EtOAc (40 mL), Pb(OAc)$_4$ (0.95 g, 2.15 mmol) was added and the mixture was stirred at room temperature for 10 minutes under $N_2$. The mixture was filtered through a celite pad and washed with EtOAc successively. The organic layer Was washed with sat. $NaHCO_3$ (50 mL×3), $H_2O$ and brine, dried ($MgSO_4$) and evaporated. The crude aldehyde was dissolved in DMF (20 mL) followed by pyridinium dichromate (2.01 g, 5.38 mmol) and the mixture was stirred at room temperature for 24 hours. The mixture was poured into $H_2O$ (30 mL) and extracted with ether (200 mL×3). The combined organic layers were washed with $H_2O$ and brine, dried ($MgSO_4$) and evaporated to give crude acid 12 (0.84 g). Crude acid 12 was dissolved in anhydrous THF (15 mL) followed by Pb(OAc)$_4$ (1.1 g, 2.58 mmol) and pyridine (0.188 mL, 2.58 mmol) and the mixture was stirred at room temperature for 30 minutes under $N_2$. The mixture was filtrated through a celite pad and washed with THF successively. After removal of solvent, the residue was purified by silica gel column chromatography (hexanes: ethyl acetate=5:1) to give acetate 13 (0.59 g, 66% from 11) as a colorless syrup.

$^1$H NMR (CDCl$_3$) δ 1.06 and 1.09 (2×s, 9 H, t-butyl), 1.88 and 2.09 (s, 3 H, OCOCH$_3$), 3.01–3.38 (m, 2 H, 4-H), 3.66–4.25 (m, 2 H, $CH_2$—OSi), 5.38–5.53 (m, 1 H, 2-H), 7.3–7.77 (m, 10 H, 2×$C_6H_5$).

(2R,5(R,S))-10[2-(t-Butyldiphenylsiloxymethyl)-1,3-oxathiolan-5-yl]-$N^4$-acetylcytosine 14 and 15

A stirred suspension of N-acetyl cytosine (6.531 g, 3.47 mmol, 1.5 eq) and $(NH_4)_2SO_4$ (10 mg, 0.075 mmol) in hexamethyldisilazane (HMDS, 25 mL) was heated to reflux under argon until a clear solution was obtained (3h). The solution was allowed to cool to room temperature and the HMDS removed under reduced pressure using anhydrous conditions.

To the solid obtained was added 1,2-dichloroethane (dried over CaH and distilled) 40 mL) followed by the acetate 13 (0.965 g, 2.314 mmol) in 1,2-dichloroethane (30 mL). This suspension was cooled in an ice/water bath to 5° C. and treated with trimethylsilyltriflate (0.7 mL, 3.47 mmol, 1.5 eq). The reaction mixture became a solution and was allowed to warm to room temperature and stir for 1.5 h at which time the reaction was judged complete by TLC. The reaction mixture was poured in ethyl acetate (300 mL) and 5% $NaHCO_3$ solution (50 mL) and allowed to be stirred for 20 min. The ethyl acetate layer was separated, washed once with sat. $NaHCO_3$ solution and twice with $H_2O$, dried, filtered, and concentrated. The residue was separated by chromatography over silica to obtain three fractions: 14, 0.2 g; 15, 0.25 g, 14+15 mix 15 major 0.15 g, total 0.6 g (50%).

14 ($\alpha$ isomer): $^1H$ NMR: ($CDCl_3$) $\delta$ 1.07 (s, 9 H, t-butyl-Si), 2.28 (s, 3 H, Ac), 3.14 (d, $J_{4a,4b}$=12.11 Hz, 1 H, 4a-H), 3.54 (dd, $J_{5,4}$=4.1 Hz, $J_{4a,4b}$=12.11 Hz, 1 H, 4b-H), 3.74 (d, $J_{2,2\text{-}CH2\text{-}OR}$=4.4 Hz, 2H, 2-$CH_2$—OR), 5.62 (t, $J_{22,2\text{-}CH2\text{-}OR}$=4.4 Hz, 1 H, 2-H), 6.35 (d, $J_{5,4}$==4.1 Hz, 1 H, 5-H), 7.3–7.85 (complex multiplet, 12 H, Ar-Si and H-5, H-6), 9.91 (bs, 1 H, NHAc); UV (MeOH) $_{max}$ 297 nm, (H+) 311 nm.

15 ($\beta$ isomer): $^1H$ NMR: ($CDCl_3$) $\delta$ 1.11 (s, 9 H, t-butyl Si), 2.24 (s, 3 H, Ac), 3.20 (dd, $J_{5,4a}$=2.4 Hz, $J_{4a,4b}$=12.5 HZ, 1 H, 4a-H), 3.56 (dd, $J_{5,4b}$=5.3 Hz, $J_{4a,4b}$=12.5 Hz, 1 H, 4b-H), 3.95 (dd, $J_{2,2\text{-}CHaOR}$=3.5 Hz, $J_{CHa,b\text{-}OR}$=11.8 Hz, 1 H, 2-$CH_1$-OR), 4.2 (dd, $J_{2,2\text{-}CHb\text{-}OR}$=3.5 Hz, $J_{2\text{-}CHa,b\text{-}OR}$=11.8 Hz, 1 H, 2-$CH_b$-OR), 5.28 (t, $J_{2,2}$-CHa,b-OR=3.5 Hz, 1 H, 2-H), 6.35 (dd, $J_{5,4a}$=2.4 Hz, $J_{5,4b}$=5.3 Hz, 1 H, 5-H), 7.21 (d, $J_{5,6}$=7.4 Hz, 1 H, H-5), 7.3–7.8 (complex multiplet, 10 H Ar-Si), 8.28 (d, $J_{5,6}$7.4 Hz, 1 H, H-6), 8.88 (bs, 1 H, NHAc); UV (MeOH) $_{max}$ 297 nm, (H+) 311 nm.

(2R,5R)-1-[2-(t-Butyldiphenylsiloxymethyl)-1,3-oxathiolan-5-yl]cytosine 16

A solution of the $\alpha$ anomer 14 (0.10 g, 0.196 mmol) in MeOH (10 mL) was treated with $NH_3$/MeOH (sat. solution 0.5 mL) and the reaction mixture stirred at room temperature until disappearance of starting material was complete (3 hr). The reaction mixture was then concentrated and the residue crystallized from hexane/$CH_2Cl_2$ to give 0.07 g (76%) of 16 as a white crystalline solid. $^1H$ NMR: ($CDCl_3$) $\delta$ 1.06 (s, 9 H, t-butyl Si), 3.12 (dd, $J_{5,4a}$ 1.1 Hz, $J_{4a,4b}$=12.3 Hz, 1 H, 4a-H), 3.51 (dd, $J_{5,4b}$=4.8 Hz, $J_{4a,4b}$=12.3 Hz, 1 H, 4b-H), 3.73 (d, $J_{2,2\text{-}CH2\text{-}OR}$=4.83 Hz, 2-$CH_2$-OR), 5.55 (t, $J_{2,2\text{-}CH2\text{-}OR}$=4.83 Hz, 1 H, 2-H), 5.67 (d, $J_{5,6}$=7.4 Hz, 1 H, H-5), 5.97 (b, 2 H, $NH_2$), 6.41 (dd, $J_{5,4a}$=1.1 Hz, $J_{5,4b}$=4.8 Hz, 1 H, 5-H), 7.3–7.8 (complex multiplet, 11 H, Ar-Si and H-6); UV (MeOH) $_{max}$ 271 nm, (H+) 283 nm.

(2R,5S)-1-[2-(Butyldiphenylsiloxymethyl)-1,3-oxathiolan-5-yl]cytosine 17

A solution of the $\beta$ anomer 15 (0.15 g, 0.294 mmol) in MeOH (10 mL) was treated with $NH_3$/MeOH (sat. solution 0.5 mL) and the reaction mixture was allowed to stir at room temperature until the disappearance of starting material was observed (3 h). The reaction mixture was concentrated under reduced pressure and the residue purified by preparative TLC using 5% MeOH/$CHCl_3$/0.5$NH_4OH$ as eluant. The material obtained from the plate gave 13 as a solid on trituration with Hexane and $Et_2O$, 0.10 g (73%).

$^1H$ NMR: ($CDCl_3$) $\delta$ 1.09 (s, 9 h, t-butyl-Si), 3.13 (dd, $J_{5,4a}$=3.3 Hz, $J_{4a,4b}$=12.3 Hz, 1 H, 4a-H), 3.5 (dd, $J_{5,4a}$=5.27 Hz, $J_{4a,4b}$=12.3 Hz, 1 H, 4b-H), 3.92 (dd, $J_{2,2\text{-}CHa\text{-}OR}$=3.74 Hz, $J_{2\text{-}CHa,b\text{-}OR}$=12.8 Hz, 1 H, 2-$CH_a$-OR), 4.16 (dd, $J_{2,2\text{-}CHb\text{-}OR}$), 4.16 (dd, $J_{2,2\text{-}CHb\text{-}OR}$=3.5 Hz, $J_{2\text{-}CHa,b\text{-}OR}$=12.8 Hz, 1 H, 2-$CH_b$-OR), 5.25 (app t, $J_{2,2\text{-}CHa\text{-}OR}$=4.16 Hz, $J_{2,2\text{-}CHb\text{-}OR}$=3.5 Hz, 1 H, 2-H), 5.46 (d, $J_{5,6}$=7.4 Hz, 1 H, H-5), 5.92 (b, 2 H, $NH_2$), 6.35 (dd, $J_{5,4a}$=3.3 Hz, $J_{5,4b}$=5.27 Hz, 1 H, 5-H), 7.3–7.8 (complex multiplet, 10 H, ArSi), 7.94 (d, $J_{5,6}$=7.4 Hz, 1 H, H-6); UV (MeOH) $_{max}$ 271.5 nm, (H+) 283.5.

(2R,5R)-1-[2-Hydroxymethyl)-1,3-oxathiolan-5-yl]-cytosine 5

To a solution of the $\alpha$ anomer 16 (0.10 g, 0.213 mmol) in THF (20 mL) was added tetrabutylammonium fluoride, 1M in THF (0.24 mL, 0.24 mmol, 1.1 eq) and the reaction mixture was allowed to stir at room temperature until TLC indicated disappearance of starting material (30 min). The reaction mixture was concentrated under reduced pressure and the residue purified by preparative TLC using 12% MeOH/$CHCl_3$ as development solvent to give 0.036 g (76%) of 5 as a hygroscopic solid. $[\alpha]^{23}_D$=146.6 (c 0.55, MeOH) (for SS isomer 4 $[\alpha]^{23}_D$=−143.18 (C 0.62, MeOH)); $^1H$ NMR: (($CD_3)_2SO$) $\delta$ 3.08 (dd, $J_{5,4a}$−2.64 Hz, $J_{4a,4b}$=12.08 Hz, 1 H, 4a-H), 3,46 (dd, $J_{5,4b}$=5.05 Hz, $J_{4a,4b}$=12.08 Hz, 1 H, 4b-H), 3.54 (app t on $D_2O$ exchange goes to d, $J_{2,2OCH2\text{-}OH}$=5.05 Hz, 2 H, 2-$CH_2$-OH), 5.16 (t, $J_{2\text{-}CH2,OH}$=5.7 Hz, 1 H, 2-$CH_2$-OH), 5.53 (t, $J_{2,2\text{-}CH2\text{-}ON}$=5.05 Hz, 1 H, 2-H), 5.83 (d, $J_{5,6}$=7.47 Hz, 1 H, H-5), 6.36 (dd, $J_{5,4a}$=2.64 Hz, $J_{5,4b}$=5.05 Hz, 1 H, 5-H), 7.16 (bs, 2 H, $NH_2$), 7.63 (d, $J_{5,6}$=7.47 Hz, 1 H, H-6).

(2R,5S)-1-[2-(Hydroxymethyl)-1,3-oxathiolan-5-yl]cytosine 3

To a solution of the $\beta$ anomer 17 (0.15 g, 0.32 mmol) in THF (25 mL) was added tetrabutylammonium fluoride 1M in THF (0.35 mL, 0.35 mmol, 1.1 eq) and the reaction was allowed to stir at room temperature until TLC indicated the disappearance of starting material (30 min). The reaction mixture was concentrated under reduced pressure and the residue purified by preparative TLC using 12% MeOH/$CHCl_3$ as development solvent to give 0.055 g (75%) of 3 from ethyl ether/MeOH (trace) as a white crystalline solid. $[\alpha]^{23}_D$=−121.6 (c 1.1, MeOH) (for the S,R isomer 2 $[\alpha]^{23}_D$=120.96 (c 1.06, MeOH)); $^1H$ NMR: (($CD_3)_2SO$) $\delta$ 3.03 (dd, $J_{5,4a}$=4.4 Hz, $J_{4a,4b}$=11.86 Hz, 1 H, 4a-H), 3.43 (dd, $J_{5,4b}$=5.3 Hz, $J_{4a,4b}$=11.86 Hz, 1 H, 4b-H), 3.80 (app t on $D_2O$ exchange goes to d, $J_{2,2\text{-}CH2\text{-}OR}$=4.17 Hz, 2 H, 2-$CH_2$-OH), 5.27 (t, $J_{2\text{-}CH2,OH}$=4.6 Hz, 1 H, 2-$CH_2OH$), 5.22 (t, $J_{2,2\text{-}CH2\text{-}OH}$=4.17 Hz, 1 H, 2-H), 5.88 (d, $J_{5,6}$=7.47 Hz, 1 H, H-5), 6.21 (app t, J=5.05 and 4.84 Hz, 1 H, 5-H), 7.19 (bs, 2 H, $NH_2$), 7.89 (d, $J_{5,6}$=7.47 Hz, 1 H, H-6).

(1'S,2R)-5-formyl-2-hydroxymethyl-5-1,3-oxathiolane 18

To a solution of 9 (1.8 g, 10.11 mmol) in MeOH (30 mL), an aqueous solution (30 mL) of $NaIO_4$ (2.99 g, 14.15 mmol) was added dropwise at −10° C. over 20 min and the mixture was stirred at −10° C. for 10 min. $NaBH_4$ was added and the mixture was further stirred at −10° C. for 10 min. After filtration, the filtrate was neutralized with glacial acetic acid at −10° C. and an aqueous solution (2.99 g, 14.15 mmol) was added dropwise at −10° C. over 20 min and the mixture Was stirred at −10° C. for 10 min. Solvents were evaporated and the residue was dissolved in EtOAc (150 mL), washed with H$_2$O and brine, dried (MgSO$_4$) and evaporated to give a crude residue 18 (1.5 g) as a colorless syrup.

(1'S,2R)-2-(t-Butyldiphenylsiloxymethyl)-5-formyl-1,3-oxathiolane 19

To a solution of 18 (1.5 g, 10.13 mmol) in DMF (20 mL), imidazole (1.38 g, 20.26 mmol) and tert-butyldiphenylsilyl chloride (5.27 mL, 20.26 mmol) were added and the mixture was stirred at room temperature for 1 hour. DMF was evaporated and the residue was dissolved in EtOAc (150 mL), washed with H$_2$O and brine, dried (MgSO$_4$) and evaporated to give a crude aldehyde 19 (3.9 g).

(2R,5(R,S))=5-Acetoxy-2-(t-butyldiphenylsiloxymethyl]-,3-oxathiolane 13

The crude aldehyde 19 (3.9 g, 10.10 mmol) was dissolved in DMF (40 mL) followed by pyridinium dichromate (9.50 g, 25.25 mmol) and the mixture was stirred at room temperature for 24 hours. The mixture was poured into H$_2$O (50 mL) and extracted with ether (300 mL×3). The combined organic layers were washed with H$_2$O and brine, dried (MgSO$_4$) and evaporated to give crude acid 12 (3.0 g). Crude acid 7 (3.0 g, 7.46 mmol) was dissolved in anhydrous THF (15 mL) followed by Pb(OAc)$_4$ (3.17 g, 7.46 mmol) and pyridine (0.55 mL, 7.46 mmol) and the mixture was stirred at room temperature for 30 minutes under N$_2$. The mixture was filtrated through a celite pad and washed with THF successively. After removal of solvent, the residue was purified by silica gel column chromatography (hexanes: ethyl acetate=5:1) to give acetate 13 (2.17 g, 52% from 4) as a colorless syrup.

$^1$H NMR (CDCl$_3$) δ 1.06 and 1.09 (2×s, 9 H, t-butyl), 1.88 and 2.09 (s, 3 H, OCOCH$_3$), 3.01–3.38 (m, 2 H, 4-H), 3.66–4.25 (m, 2 H, CH$_2$-OSi), 5.38–5.53 (m, 1 H, 2-H), 7.31–7.77 (m, 10 H, 2×C$_6$H$_5$).

This invention has been described with reference to its preferred embodiments. Variations and modifications of the invention, enantiomerically pure β-L-(−)-1,3-oxathiolane-nucleosides, will be obvious to those skilled in the art from the foregoing detailed description of the invention. It is intended that all of these variations and modifications be included within the scope of the appended claims.

We claim:

1. A process for the preparation of enantiomerically pure β-L-(−)-1,3-oxathiolane nucleosides comprising preparing the 1,3-oxathiolane ring from 1,6-dideoxy-1,6-thioanhydro-L-gulose.

2. The process of claim 1 further comprising converting 1,6-dideoxy-1,6-thioanhydro-L-gulose to 2R,5(R,S)-5-(0-protected)-2-(protected-oxymethyl)-1,3-oxathiolane.

3. The process of claim 2 further comprising condensing the (2R,5R) - and (2R,5S)-5-(0-protected)-2-(protected-oxymethyl)-1,3-oxathiolane with a heterocyclic base selected from the group consisting of a purine base and a pyrimidine base.

4. The process of claim 1 further comprising the steps of preparing 1,6-thioanhydro-L-gulose from L-gulose.

5. The process of claim 4, further comprising:
   i) protecting the hydroxyl groups on L-gulose to form a 1,2,3,4-tetra-0-(protected)-6-0-(protected)-L-gulopyranoside;
   ii) converting the 1,2,3,4-tetra-0-(protected)-6-0-(protected)-L-gulopyranoside to 2,3,4-tri-0-(protected)-1-halo-6-0-(protected)-α-L-gulopyranoside;
   iii) reacting 2,3,4-trio-0-(protected)-1-halo-6-0-(protected)-α-L-gulopyranoside with a compound selected from the group consisting of potassium 0-ethyl xanthate, NaSH, and (Na)$_2$S, to form 2,3,4-tri-0-(protected)-1,6-dideoxy-1,6-thioanhydro-L-gulose; and
   iv) deprotecting 2,3,4-tri-0-(protected)-1,6-dideoxy-1,6-thioanhydro-L-gulose to produce 1,6-thioanhydro-L-gulose.

6. The process of claim 2 further comprising:
   i) protecting the 2, 3, and 4-hydroxyl groups of 1,6-thioanhydro-L-gulose to produce 2,3,4-0-(tri-protected)-1,6-dideoxy-1,6-thioanhydro-L-gulose;
   ii) deprotecting the 2 and 3 positions of 2,3,4-0-(tri-protected)-1,6-dideoxy-1,6-thioanhydro-L-gulose to form a 4-0-protected-1,6-dideoxy-1,6-thioanhydro-L-gulose;
   iii) oxidatively cleaving the glycol of 4-0-protected-1,6-dideoxy-1,6-thioanhydro-L-gulose to the corresponding dialdehyde; and
   iv) oxidizing the dialdehyde to (2R,5(R,S)-2-(protected -oxymethyl)-1,3-oxathiolane-5-carboxylic acid.

7. The process of claim 6, wherein the (2R,5(R,S)-2-(protected-oxymethyl)-1,3-oxathiolane-5-carboxylic acid is reacted with Pb(0-acetate)$_4$ to produce (2R,5R)- and (2R,5S)-5-acetoxy-2-(protected-oxymethyl)-1,3-oxathiolane.

8. The process of claim 3, wherein the heterocyclic base is selected from the group consisting of adenine, hypoxanthine, guanine, N$^6$-alkylpurines, N$^6$-benzylpurine, N$^6$-halopurine, N$^6$-vinylpurine, N$^6$-acetylenic purine, N$^6$-acyl purine, N$^6$-hydroxyalkyl purine, 2,6-dihalopurine, N$^6$-thioalkyl purine, thymine, cytosine, 6-azapyrimidine, 2-mercaptopyrimidine, uracil, 5-alkylpyrimidines, 5-benzylpyrimidines, 5-halopyrimidines, 5-vinylpyrimidine, 5-acetylenic pyrimidine, 5-acyl pyrimidine, 5-hydroxyalkyl pyrimidine, 5-azapyrimidine, 5-thioalkyl pyrimidine, 6-thiophenyl pyrimidine, and 6-selenophenyl pyrimidine.

9. The process of claim 8, wherein the heterocyclic base is thymine.

10. The process of claim 1, wherein the 1,3-oxathiolane nucleoside is β-L-(−)-1-[(2β,4β)-2-(hydroxymethyl)-4-(1,3-thioxolane)]cytosine.

* * * * *